(12) United States Patent
D'Alessio et al.

(10) Patent No.: US 6,369,096 B1
(45) Date of Patent: *Apr. 9, 2002

(54) BENZYLOXY PRODIGIOSINE COMPOUNDS

(75) Inventors: Roberto D'Alessio, Cinisello Balsamo; Ermes Vanotti; Alberto Bargiotti, both of Milan; Marcellino Tibolla, Senago; Mario Ferrari, Milan; Anna Maria Isetta, Rho; Francesco Colotta, Milan, all of (IT)

(73) Assignee: Pharmacia & Upjohn S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,455

(22) PCT Filed: Jan. 21, 1999

(86) PCT No.: PCT/EP99/00415

§ 371 Date: Oct. 7, 1999

§ 102(e) Date: Oct. 7, 1999

(87) PCT Pub. No.: WO94/40069

PCT Pub. Date: Aug. 12, 1997

(30) Foreign Application Priority Data

Feb. 9, 1998 (GB) .............................................. 9802745

(51) Int. Cl.$^7$ ................... A61K 31/4025; C07D 403/14
(52) U.S. Cl. ........................................ 514/422; 548/518
(58) Field of Search ........................... 548/518; 514/422

(56) References Cited

U.S. PATENT DOCUMENTS

| 5,691,334 A | 11/1997 | Doria et al. ............. 514/235.5 |
| 5,847,127 A | 12/1998 | D'Alessio et al. .......... 544/141 |

FOREIGN PATENT DOCUMENTS

WO    WO 95/17381    6/1995

*Primary Examiner*—Laura L. Stockton
(74) *Attorney, Agent, or Firm*—Oblon, Spivak, McClelland, Maier & Neustadt, P.C.

(57) ABSTRACT

A compound, having utility as an immunomodulating agent, which is a prodigiosine of formula (I):

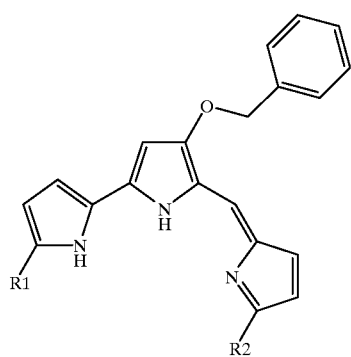

wherein
  R1 is hydrogen or $C_1$–$C_5$ alkyl; and
  R2 is a $C_1$–$C_5$ alkyl;
or a pharmaceutically acceptable salt thereof.

14 Claims, No Drawings

BENZYLOXY PRODIGIOSINE COMPOUNDS

This application is a 371 of PCT/EP99/00415 filed Jan. 21, 1999.

The present invention relates to novel benzyloxy prodigiosine compounds, to a process for their preparation, to pharmaceutical compositions containing them and to their use as therapeutic agents, in particular as immunomodulating agents.

International application WO 95/17381 discloses 2,2'-bi-1H-pyrrole compounds endowed with high in vitro immunosuppressive activity. However such compounds, similarly to other known prodigiosine compounds, are characterized by high lipophylicity, low aqueous solubility and consequently low bioavailability.

Moreover, the task to combine in the same prodigiosine molecule a high immunosuppressive activity and adequate hydrosolubility cannot be achieved by merely introducing hydrophilic groups into the structure of in vitro active immunosuppressants, as in most cases this strategy results in a significant loss of immunosuppressive activity. In fact, as known in the art, the therapeutic efficacy of all drugs is thoroughly influenced by different parameters that can affect their bioavailability. Object of the present invention is to provide novel prodigiosine compounds endowed with improved bioavailability.

The present invention is based on the discovery that a sub-genus of compounds disclosed in WO 95/17381, besides possessing good bioavailability, have in vivo high immunosuppressive activity.

Object of the present invention are novel compounds which are 2-(1H-pyrrol-2-yl)-5[(2H-pyrrol-2-ylidene) methyl]-1H-pyrroles i.e. prodigiosine compounds, having the following formula (I)

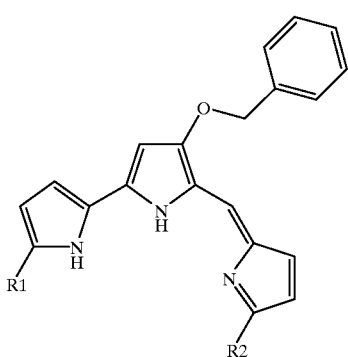

(I)

wherein

R1 is hydrogen or a $C_1$–$C_5$ alkyl; and

R2 is $C_1$–$C_5$ alkyl;

or pharmaceutically acceptable salts thereof.

The present invention includes within its scope all possible isomers, stereoisomers and optical isomers and their mixtures, and the metabolites and the metabolic precursors or bioprecursors of the compounds of formula (I).

The compounds of the invention can be represented also by the following tautomeric formula (Ia)

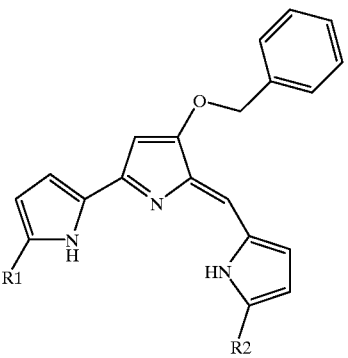

(Ia)

wherein R1 and R2 are as defined above.

Accordingly, the chemical compounds provided by the present invention are named throughout the description of the invention according to the chemical nomenclature provided for the compounds of either formula (I) or (Ia), on the basis of the structural evidence validated by people skilled in the art.

The alkyl groups may be branched or straight chain groups.

R1 as alkyl group is preferably methyl or ethyl.

R2 is preferably a methyl, ethyl, propyl, isopropyl, butyl or pentyl group.

Examples of pharmaceutically acceptable salts of the compounds of the invention are the salts with inorganic, e.g. hydrochloric, hydrobromic and sulphuric acids and with organic acids, e.g. citric, tartaric, maleic, malic, fumaric, methanesulphonic and ethanesulfonic acids.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are those wherein, in formula (I),

R1 is hydrogen or methyl;

R2 is a $C_1$–$C_5$ alkyl.

Examples of particularly preferred compounds of the invention are:

4-benzyloxy-5-[(5-methyl-2H-pyrrol-2-ylidene)methyl]-2,2'-bi-1H-pyrrole;

4-benzyloxy-5-[(5-ethyl-2H-pyrrol-2-ylidene)methyl]-2,2'-bi-1H-pyrrole;

4-benzyloxy-5-[(5-propyl-2H-pyrrol-2-ylidene)methyl]-2,2'-bi-1H-pyrrole;

4-benzyloxy-5-[(5-isopropyl-2H-pyrrol-2-ylidene)methyl]-2,2'-bi-1H-pyrrole;

4-benzyloxy-5-[(5-butyl-2H-pyrrol-2-ylidene)methyl]-2,2'-bi-1H-pyrrole;

4-benzyloxy-5-[(5-pentyl-2H-pyrrol-2-ylidene)methyl]-2,2'-bi-1H-pyrrole;

5'-methyl-4-benzyloxy-5-[(5-methyl-2H-pyrrol-2-ylidene) methyl]-2,2'-bi-1H-pyrrole;

5'-methyl-4-benzyloxy-5-[(5-ethyl-2H-pyrrol-2-ylidene) methyl]-2,2'-bi-1H-pyrrole;

and the pharmaceutically acceptable salts thereof, in particular the hydrochlorides, hydrobromides and methanesulphonates.

A further object of the present invention is to provide a compound of formula (I), as defined above, for use in a method of treatment of the human or animal body by therapy, in particular as an immunomodulating agent, especially as an immunosuppressive agent.

Object of the present invention is also to provide a pharmaceutical composition comprising a pharmaceutically acceptable carrier and/or diluent and as an active principle a compound of formula (I), as herein defined, or a pharmaceutically acceptable salt thereof.

The present invention also provides a method of treating a mammal, including humans, in need of an immunomodulating agent, said method comprising administering to said mammal an effective amount of a compound of formula (I), as herein defined, or a pharmaceutically acceptable salt thereof.

The compounds of formula (I) and the pharmaceutically acceptable salts thereof can be obtained by an analogy process.

According to a preferred embodiment of the invention a compound of formula (I) and the salts thereof can be prepared by a process comprising reacting a compound of formula (II)

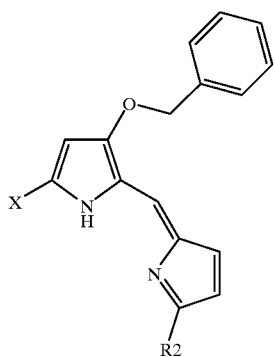

(II)

wherein
R2 is as defined above and X is a leaving group, with a compound of formula (III)

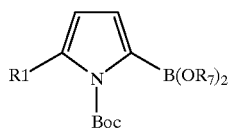

(III)

wherein
R1 is as defined above and R7 is hydrogen or a lower alkyl chain;
and, if desired, salifying a compound of formula (I) and/or, if desired, converting a salt of a compound of formula (I) into a free compound and/or, if desired, separating a mixture of isomers of a compound of formula (I) into the single isomers.

When R7 is a lower alkyl chain, it is preferably a $C_1$–$C_4$ alkyl chain, for instance methyl, ethyl or isopropyl. In a compound of general formula (II), the leaving group X can be for instance a trifluoromethane-sulphonate group or a halogen such as chlorine, bromine or iodine.

The reaction between a compound of formula (II) and a compound of formula (III) may be carried out in a suitable organic solvent such as tetrahydrofurane, dioxane, dimethoxyethane, DMF, toluene, methanol, ethanol, water or mixtures thereof, in the presence of a suitable palladium (0) catalyst, in the presence of a basic agent, such as $K_2CO_3$, $Na_2CO_3$, $NaHCO_3$, $K_3PO_4$, NaOAc, KOH, NaOH, Ba(OH)$_2$, EtONa, Bu$_4$NF, Et$_3$N, at a temperature varying between about 60° C. and about 120° C., for a time of about 1 hour to about 3 days.

A wide range of palladium (0) catalysts can be used such as for instance Pd(PPh$_3$)$_4$, PdCl$_2$(PPh$_3$)$_2$, Pd(OAc)$_2$ plus PPh$_3$ or other ligands as described for example in Chem. Rev. 95, 2457 (1995).

Optionally, salt such as LiCl, LiBr, KCl, KBr can be added to stabilize the catalyst.

According to a preferred embodiment of the invention, when in a compound of formula (II) the leaving group X is trifluoromethanesulfonate, a preferred catalyst is Pd(PPh$_3$)$_4$ in the presence of sodium or potassium carbonate, and the reaction can be performed in dioxane or toluene, at a temperature varying between about 65° C. and about 90° C., for a time from about 5 hours to about 24 hours.

Also the optional salification of a compound of formula (I) as well as the conversion of a salt into the free compound and the separation of a mixture of isomers into the single isomers may be carried out by conventional methods. For example, the separation of optical isomers may be carried out by salification with an optically active base or acid and by subsequent fractional crystallization of the diastereoisomeric salts, followed by recovering of the optically active isomeric acids or, respectively, bases.

A compound of formula (II) can be obtained from a compound of formula (IV)

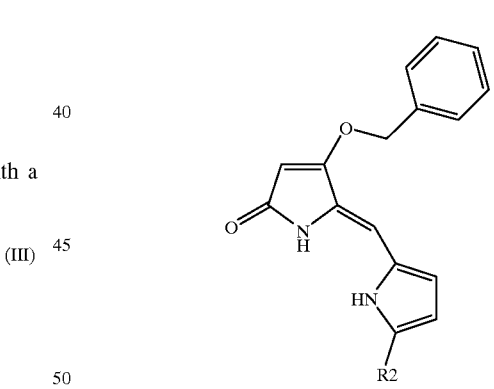

(IV)

wherein
R2 is as defined above, by means of an opportune reagent such as for instance trifluoromethane-sulfonic anhydride or a halogenating agent such as POCl$_3$, POBr$_3$, POCl(OEt)$_2$/TMSI in an inert organic solvent such as dichloromethane, dichloroethane, acetonitrile, optionally in the presence of an organic base such as Et$_3$N or pyridine, at a temperature varying between about −20° C. and about 50° C. (as described for example in PCT/EP 97/00368).

The compounds of formula (III) can be prepared as described in published procedures, as for instance in J. Org. Chem. 46, 157 (1981) and Synthesis, 613 (1991).

The compounds of formula (IV) can be prepared reacting a compound of formula (V)

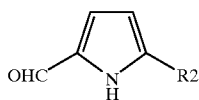

wherein
R2 is as defined above,
with 4-benzyloxy-3-pyrrolin-2-one (VI)

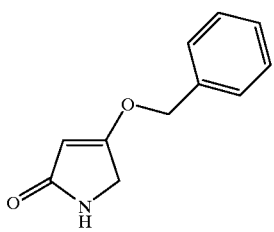

The condensation between a compound of formula (V) and the compound of formula (VI) can be performed by acidic or basic catalysis, in a solvent such as water, methanol, ethanol, dioxane, THF, DMF, DMSO or mixtures thereof, at a temperature varying from about 25° C. to about 120° C., in a time ranging from about 1 hour to about 24.

A acidic catalyst can be e.g. an inorganic acid such as HCl, HBr, $H_2SO_4$, $H_2NO_3$ or an organic acid such as, for instance, p-toluensulphonic acid, methansulphonic acid, trifluoromethan-sulphonic acid or trifluoroacetic acid. As well, a basic catalyst can be e.g. an inorganic base such as NaOH, KOH, $K_2CO_3$, $Ba(OH)_2$, NaH or an organic base such as, for instance, t-BuOk, MeLi, BuLi, LDA.

The compounds of formula (V) can be prepared, for example, by Vilsmeier formylation of the compounds of formula (VII)

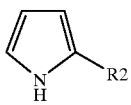

wherein R2 is as defined above, according to well known chemical procedures.

The compounds of formula (VII) are known compounds or may be prepared using mere variations of published procedures, for example those reported in the following chemical literature: Tetrahedron 32, 1851 (1976); J.Org.Chem. 53, 1410 (1988); J. Org.Chem. 28, 857 (1963); J. Am. Chem. Soc. 84, 4655 (1962); Ann. 450, 181 (1926); Ber. 99, 1414 (1966).

The compound of formula (VI) are commercially available or can be synthesized as described for example in Synthesis, 391 (1992) and Tetrahedron Letters 25, 1871 (1984).

When in the compounds of formula (I), and in the intermediate products thereof, groups are present which need to be protected before submitting them to the here above illustrated reactions, they may be protected before the reactions take place and then deprotected, according to well known methods in organic chemistry.

The compounds of formulae (I) and the pharmaceutically acceptable salts thereof are herein defined as the "compounds of the present invention", the "compounds of the invention" and/or the "active principles of the pharmaceutical compositions of the invention".

Pharmacology

The compounds of the invention have immunomodulating, in particular immunosuppressive, in vivo activity as found for example in the "Delayed-Type Hypersensitivity" assay and a remarkable bioavailability after oral administration as compared to products described in the prior art.

Comparative in Vivo Activity Evaluation by DTH Assay

The immunosuppressive activity of the compounds of the invention was evaluated in vivo by DTH (Delayed-Type Hypersensitivity) assay. According to the test, sheep red blood cells (SRBC) ($1 \times 10^5$ cells) suspended in 500 mcL saline, were injected i.v. into the tail vein of female C57 Bl/6 mice (8–9 week old). Five days later $1 \times 10^8$ SRBC suspended in 50 mcL saline were injected into the left hind footpad. The increase in footpad thickness was measured with a dial micrometer 24 h after challenge. The test compounds were given daily for six days at different doses starting on the day of priming. Activity was expressed as ED30 (dose able to reduce by 30% the thickness increase compared to controls).

In Vivo Bioavailability Evaluation

Aim of the study is to determine the pharmacokinetics and the oral bioavailability of the instant prodigiosine compounds in rats.

Species/strain/sex: rat/Lewis/male

No. formulations: 1 oral; 1 intravenous

No. animals/formulation: 3+2 controls (+an ulterior rat treated with the iv formulation); total 9

Dosages: iv: 1 mg salt/kg; oral: 10 mg salt/kg

Vehicles: iv: a solution at the conc. of 5 mg/ml in PEG 400/Tween 80 (6:1 v:v) was prepared, then diluted with dextrose at the final concentration of 0.5 mg/ml; oral: a solution at the concentration of 5 mg/ml in Cremophor ELP/EtOH abs (6.5:3.5 v:v) was prepared, then diluted with saline at the final concentration of 1 mg/ml Experimental: Three cannulated rats/formulation were treated. One rat/formulation was only treated with the vehicle, as basal sample. The intravenous administration was given into the caudal vein as bolus; the oral administration by gastric gavage as solution. Blood was withdrawn from the superior vena cava from each rat and collected into heparinized tubes at the following times: 2' (only for the iv route), 5', 15', 30'; 1, 2, 4, 6, 8, 24 and 32 h post-dosing. Plasma was immediately obtained by centrifugation (10000 rpm for 3 min) and stored in labelled tubes at −30° C. till analysis.

Analytical assay: the extraction of the compounds was performed by protein precipitation by adding 100 mcl of acetonitrile to 25 mcl of plasma. The concentrations of the compounds (as free bases) in plasma were determined by LC-MS method. Column: APEX CN RP 5 mc, 10×4 mm (Jones chromatography); mobil phase: 70% acetonitrile/30% 1 mM ammonium formate +0.01% triethylamine adjusted to pH 2.0 with formic acid; flow rate: 1 ml/min; injection volume: 10 mcL; oven temperature: 45° C.; MS detection by APCI using MRM positive ion; MRM transition: 330 m/z>239 m/z, retention time: 1.4 min; LLOQ: 5.03 ng/ml; ULOQ: 10060 ng/ml. Bioavailability is expressed in following Table 1 as F %. ClogP is a lypophylic index, related to octanol/water partition coefficient.

Following Table 1 shows the results obtained for two representative compounds of the invention in comparison with a closely-related prior art compound.

TABLE 1

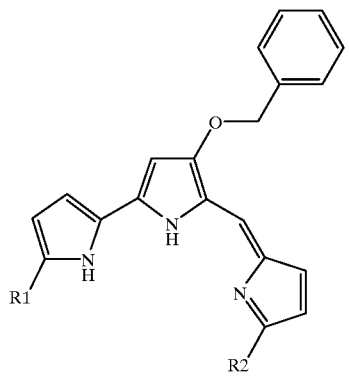

| Compound | R1 | R2 | ClogP | DTH ED30 (mg/kg) | | F % |
|---|---|---|---|---|---|---|
| | | | | iv | os | |
| PNU 168727 | H | —CH$_3$ | 3.98 | 1.7 | 5.3 | 35 |
| PNU 169417 | H | —C$_5$H$_{11}$ | 5.64 | 1.1 | 4.4 | 18 |
| PNU 156804 | H | —C$_{11}$H$_{23}$ | 8.02 | 0.44 | 18.7 | 7 |

In Table 1:

PNU 168727 means 4-benzyloxy-5-[(5-methyl-2H-pyrrol-2-ylidene)methyl]-2,2'-bi-1H-pyrrole, hydrochloride;

PNU 169417 means 4-benzyloxy-5-[(5-pentyl-2H-pyrrol-2-ylidene)methyl]-2,2'-bi-1H-pyrrole, hydrochloride;

PNU 156804 means 4-benzyloxy-5-[(5-undecyl-2H-pyrrol-2-ylidene)methyl]-2,2'-bi-1H-pyrrole, hydrochloride.

PNU 156804 is the most active compound disclosed by WO 95/17381, as shown on page 32 of such prior art reference where it is coded as FCE 29002.

In view of their valuable biological properties the compounds of the invention can therefore be useful in mammals, including humans, as immunosuppressive agents for the prevention and treatment of rejection phenomena associated with tissue and organ transplantations, graft-versus-host diseases and autoimmune diseases. A mammal, comprising humans, in need of an immunomodulating agent, in particular of an immunosuppressive agent, can therefore be treated by a method comprising the administration thereto of a therapeutically effective amount of a compound of the invention or a pharmaceutically acceptable salt thereof. The condition of the human or animal patient can thus be improved.

Preferred cases of organ and tissue transplants which can be successfully treated by the compounds of the invention, here above described, are, for example, the cases of heart, kidney, bone marrow, lung, liver, and multiple organ transplantations.

Preferred cases of autoimmune diseases which can be successfully treated by the compounds of the invention, here above described, are for example, the cases of rheumatoid arthritis, systemic lupus erythematosus, juvenile diabetes, autoimmune haemolytic anaemia, miastenia gravis, multiple sclerosis, psoriasis, ulcerative colitis, idiopathic thrombocytopenic purpura, active chronic hepatitis, glomerulonephritis, idiopathic leucopenia, primary biliary cirrhosis, thyroiditis, thyrotoxicosis, dermatomyositis, discoid lupus erythematosus, psoriatic arthritis, regional enteritis, nephrotic syndrome, lupus nephritis, lupoid hepatitis, Sjögren's syndrome, Goodpasture's syndrome, Wegener's granulomatosis, scleroderma, Sezary's disease, uveitis and mumps orchitis. Typically rheumatoid arthritis, systemic lupus erythematosus, juvenile diabetes, miastenia gravis, multiple sclerosis and psoriasis.

The therapeutic regimen for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the acute treatments.

For maintenance regimens the oral or parenteral, e.g. intramuscular or subcutaneous, route is preferred.

For these purposes the compounds of the invention, can be administered orally at doses ranging e.g. from about 0.5 to about 10 mg/kg of body weight per day in adult humans.

Doses of active compounds ranging e.g. from about 0.25 to about 5 mg/kg of body weight per day can be used for the parenteral administration and for intravenous injection or infusion in adult humans. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention, may be administered in the form of aqueous or oily solutions or suspensions, tablets, pills, gelatine capsules, syrups, drops or suppositories.

Thus, for oral administration, the pharmaceutical compositions, containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixture; dyestuffs; sweeteners; wetting agents, such as lecithin, polysorbates, laurylsulphates and in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

The present invention also provides products containing a compound of formula (I), or a pharmaceutically acceptable salt thereof, and an additional drug as a combined preparation for simultaneous, separate or sequential use in immunosuppressive therapy in mammals.

Such additional drug can be for instance a corticosteroid, an immunosuppressive or an anti-tumor agent, or mixtures of two or more of them.

The term "antitumor agent" is meant to comprise both a single anti-tumor drug and "cocktails", i.e. a mixture of such drugs according to clinical practice.

Examples of anti-tumor agents that can be formulated in immunosuppressive therapy with a compound of formula (I), include methotrexate and cyclophosphamide and mixtures thereof.

The term "immunosuppressive agent" is meant to comprise both a single immunosuppressive drug and "cocktails", i.e. a mixture of such drugs according to clinical practice.

Examples of immunosuppressive agents that can be formulated with a compound of formula (I), include for instance one of the following:

cyclosporin A or cyclosporin C, a non-polar cyclic oligopeptide; FK506, a fungal macrolide immunosuppressive; azathioprine, or 6-[(1-Methyl-4-nitro-1H-imidazol-5-yl)-thio]1H-purine; methotrexate; rapamycin, a fungal macrolide immunosuppressive; mycophenolate mofetil, or 6-(4-hydroxy-6-methoxy-7-methyl-3-oxo-1,3-dihydroisobenzofuran-5-yl)-4-methyl-4-(E)-hexenoic acid 2-(4-morpholinyl)-ethyl ester; an immunosuppressive glucocorticoid, such as prednisone or dexamethasone; and/or polyclonal, such as a anti-human thymocite antibody or a monoclonal such as a anti-human CD3 antibody; or a mixture of two or more thereof.

It has to be noted that co-administration of an immunosuppressive agent, as defined above, and at least one benzyloxy prodigiosine compound of formula (I), or a pharmaceutically acceptable salt thereof, as herein defined, produces a potentiated immunosuppressive activity in synergistic way, thus giving a superadditive immunosuppressive effect, i.e. effect which is greater than the sum of the actions of the individual components. A person skilled in the art will appreciate that such superadditive immunosuppressive effect allows administration of lower dosage levels of immunosuppressive agents, thus lowering the side effects caused by commonly used immunosuppressant agents.

Accordingly, the present invention also provides a pharmaceutical composition for use in immunosuppressive therapy in mammals, including humans, comprising:

(a) an immunosuppressive agent in a pharmaceutically acceptable carrier and/or excipient, and (b) at least one compound of formula (I), as defined above, or a pharmaceutically acceptable salt thereof in a pharmaceutically acceptable carrier and/or excipient, in amounts to produce a superadditive immunosuppressant effect.

A further aspect of the present invention is an immunosuppressive therapy method for use in mammals, including humans, in need thereof, the method comprising administering to said mammal (a) an immunosuppressive agent and (b) at least one compound of formula (I), as defined above, or a pharmaceutically acceptable salt thereof, in amounts effective to produce a superadditive immunosuppressive effect.

In view of the combined therapeutic effect obtainable by such combined preparation, lower doses of immunosuppressive agents can be used.

Accordingly, the invention also provides a method for lowering the side effects, such as nephrotoxicity and/or hepatotoxicity, caused by immunosuppressive therapy with an immunosuppressive agent in mammals, including humans, in need thereof, the method comprising administering to said mammal a combination preparation comprising (a) said immunosuppressive agent and (b) at least one compound of formula (I), as defined above, or a pharmaceutically acceptable salt thereof, in a quantity effective to produce a superadditive immunosuppressive effect.

In the combined preparations, pharmaceutical compositions and method of treatment according to the present invention only one compound of formula (I), as defined above, or a pharmaceutically acceptable salt therapy, is preferably used. The combination preparation according to the invention can also include combination packs or compositions in which the constituents are placed side by side and can therefore be administered simultaneously, separately or sequentially to one and the same mammal, including humans.

The benzyloxy prodigiosine compounds of formula (I) and the pharmaceutically acceptable salts thereof have also been found to be active in treating adult-T-cell leukemia-lymphoma, in particular brought on by infection with HTLV-I in mammals, including humans. Such therapeutic activity of the compounds of the invention is proven for instance by the fact that they have been found to be active in inhibiting selectively the IL-2 induced activation and expansion of murine and human T-cells, showing thus a pharmacological profile consistent with the therapy of the IL-2 dependent ATL.

Inhibition of IL-2 Proliferation Induced Activity

The Th murine cells D10-G4.1 (ATCC TIB 224) are IL-2 dependent for their growth. They are cultured in complete RPMI 1640 medium enriched with rhIL-2 (6 ng/ml) and ConA (6 ng/ml).

For testing the inhibitory effects of the compounds of the invention on IL-2 activity, D 10 cells are washed twice with complete medium, resuspended at $10^5$ cells/ml in the same medium and triplicately distributed ($10^4$ cells/well) in flat bottomed 96 well plates. 50 ml of rhIL-2 and 50 ml of the test compound at different concentrations are simultaneously added to the cells. The cultures are then incubated at 37° C. in a humidified 5% $CO_2$ incubator for 48 h, the last 18 h in the presence of 0.2 □Ci of $^3$H-TdR.

Uptake of 3H-TdR in the cells (cpm) is taken as a measure of cell proliferation.

For instance for the representative compound of the invention 4-benzyloxy-5-[(5-methyl-2H-pyrrol-2-ylidene)methyl]-2,2'-bi-1H-pyrrole (internal code PNU 168727) the following activity data were obtained.

| Compound | ng/ml | $^3$HTdR uptake * | % inhibition vs vehicle |
|---|---|---|---|
| PNU 168727 | 30 | 52 (8) | 100 |
| | 10 | 8100 (34) | 87 |
| | 3 | 54594 (424) | 11 |
| | 1 | 58245 (1133) | 5 |
| vehicle | — | 61231 (1193) | |

* mean cpm from triplicate wells (SE)

In treating a adult-T-cell leukemia-lymphoma one or more compound of formula (I), as defined above, can be administered alone or in association with an anti-tumor agent. Preferably a single compound of formula (I) is used. Accordingly, the present invention provides a compound of formula (I), as herein defined, or a pharmaceutically acceptable salt thereof for use in treating adult-T-cell leukemia-lymphoma.

A further object of the present invention is a method of treating mammals, including humans, suffering from adult-T-cell leukemia-lymphoma, said method comprising administering a therapeutically effective amount of a compound of formula (I), as herein defined, or a pharmaceutically acceptable salt thereof.

Object of the present invention is also to provide a pharmaceutical composition having activity against adult-T-cell leukemia-lymphoma comprising a compound of formula (1), as herein defined, or a pharmaceutically acceptable salt thereof, as an active ingredient, and a pharmaceutically acceptable carrier or diluent.

A further object of the present invention is to provide a combined method of treatment of adult-T-cell leukemia-lymphoma in mammals, including humans, in need thereof, said method comprising administering thereto a compound of formula (I), or a pharmaceutically acceptable salt thereof, and an anti-tumor agent, in amounts and close enough together in time sufficient to produce a therapeutically useful effect. The present invention also provides a product containing a compound of formula (I), or a pharmaceutically acceptable salt thereof, and an anti-tumor agent as a combined preparation for simultaneous, separate or sequential use in adult-T-cell leukemia-lymphoma therapy.

The term "anti-tumor agent" is meant to comprise both a single anti-neoplastic agent and "cocktails", i.e. a mixture of such drugs according to clinical practice.

An anti-neoplastic agent in treating adult-T-cell leukemia lymphoma can be for example an agent selected from the group consisting of an antineoplastic vinca alkaloid, an antineoplastic antibiotic, an antineoplastic antimetabolite, an antineoplastic platinum coordination complex, an antineoplastic taxane compound, an antineoplastic ceramide compound, an antineoplastic distamycin compound, an antineoplastic epidophyllotoxin compound and an antineoplastic topoisomerase I inhibitor. Examples of specific antineoplastic agents, according to the invention, which are administered with a compound of formula (I), are: vincristine, vinblastine, etoposide, tallimustine-amidoxime, 3-(1-methyl-4-(1-methyl-4-(1-methyl-4- (4,N,N-bis(2-chloroethyl)aminobenzene-1-carboxamido)pyrrole-2-carboxamido)pyrrole-2-carboxamido)pyrrole-2-carboxamido)proprionamidoxime, (2S-RR-4E)-1,3-dihydroxy-2-tetradecanoylamido-4-octadecene, paclitaxel, docetaxel, 7-epitaxol, 7-epitaxotere, epirubicin, doxorubicin, cyclophosphamide, idarubicin, 4'-iodoxorubicin, daunorubicin, actinomicin D, bleomycin, plycamicin, mitomycin, camptothecin, 9-aminocamptothecin, camptothecin 11 (CPT 11), topotecan, metotrexate, cytarabine, azauridine, azarabine, fluorodeoxyuridine, deoxycoformycin, mercaptopurine, cisplatin and carboplatin.

In particular they are epirubicin, doxorubicin, cyclophosphamide, 9-aminocamptothecin and camptothecin 11. The dosage of a compound of the invention to be administered to a patient suffering from adult-T-cell leukemia-lymphoma, in particular brought on by infection with HTLV-I, will vary with the precise nature of the conditions being treated and the recipient of the treatment.

A therapeutically effective dosage of the compounds of formula (I), for example the compound 4-benzyloxy-5-[(5-methyl-2H-pyrrol-2-ylidene]-2,2'-bi-1H-pyrrole hydrochloride (PNU 168727), is in the range of about 0.03 to about 1.5 mg/kg, preferably about 0.06 mg/kg to about 0.7 mg/kg when given i.v. whereas the dose of the same compound for oral administration in adult humans is in general from about 0.3 mg/kg/day to about 15 mg/kg/day.

The dosage of a compound of formula (I) and of an antitumor agent, in case of combined therapy, to be used is, of course, dependent on various factors such as the organism to be treated (e.g., human or animal, age, weight, general state of health), the severity of the symptoms, the disorder to the accompanying treatment with other pharmaceuticals, or the frequency of the treatment. The dosages are in general administered several times per day and preferably once to three times per day. The effective amounts of the antitumor agent are in general those commonly used in therapy, as known to those skilled in the art. However, the amounts of the individual active compounds should be within the range given above, e.g. within the tolerable, efficacious dosage range for the organism to be treated.

The oral route is employed, in general, for all conditions requiring the compounds of the invention. Preference is given to intravenous injection or infusion for the acute treatments. For maintenance regimens the oral or parenteral, e.g. intramuscular or subcutaneous, route is preferred. The nature of the pharmaceutical preparations and compositions according to the invention will of course depend upon the desired route of administration.

The compositions may be formulated in the conventional manner with the usual ingredients, for instance as described above.

The following examples illustrate but do not limit the invention.

Example 1

Compound (IV)

To a solution of 2-formyl-5-methylpyrrole (4 g; 36.65 mmols) and 4-benzyloxy-3-pyrrolin-2-one (8.24 g; 43.78 mmols) in DMSO (65 ml) 2N sodium hydroxyde (45 ml) was added under nitrogen atmosphere and the mixture was stirred at 60° C. for 8 hours. After dilution with water (200 ml) the yellow suspension was filtered. The crude material was taken up in ethyl acetate, stirred and filtered to give 4-benzyloxy-5-(5-methyl-1H-pyrrol-2-yl-methylene)-1,5-dihydro-pyrrol-2-one (7.7 g; 27.49 mmols) as a 4:1 Z:E mixture. Yield: 75%

$^1$NMR (400 mhz, CDCl$_3$), ppm: 1.73 (3H, s, E), 2.19 (3H, s, Z), 5.07 (2H, s, Z), 5.16 (2H, s, E), 5.22 (1H, s, Z), 5.46 (1H, s, E), 5.67 (1H, t, J=3.0 Hz, E), 5.80 (1H, t, J=3.0 Hz, Z), 6.08 (1H, s, Z), 6.09 (1H, s, E), 6.20 (1H, t, J=3.0 Hz, E), 6.46 (1H, t, J=3.0 Hz, Z), 7.2–7.6 (5H, m, E+Z), 9.34 (1H, s, E+Z), 9.86 (1H, bs, E) , 10.69 (1H, bs, Z).

Example 2

Compound (II)

To a suspension of 4-benzyloxy-5-(5-methyl-1H-pyrrol-2-yl-methylene)-1,5-dihydro-pyrrol-2-one (3g; 10.70 mmols) in dichloromethane (160 ml) at −10° C. trifluoromethansulphonic anhydride (2.16 ml; 12.84 mmols) was added dropwise under nitrogen atmosphere. After stirring at this temperature for 30'the reaction mixture was poured into a cold 5% NaHCO solution (300 ml) and extracted with dichloromethane (2×100 ml). The collected organic extracts were shaken with brine, anhydrified over anhydrous sodium sulphate and evaporated to dryness to give 2-trifluoromethane-sulphonyloxy-4-benzyloxy-5-[(5-methyl-2H-pyrrol-2-ylidene)-methyl]-1H-pyrrole (4.23 g; 10.26 mmols) as a yellow solid. Yield: 96%.

$^1$NMR (400 mhz, CDCl$_3$), ppm: 2.67 (3H, s), 5.05 (2H, s), 5.46 (1H, s), 6.04 (1H, d, J=3.7 Hz), 6.64 (1H, d, J=3.7 Hz), 7.08 (1H, s), 7.41 (5H, m), 10.8 (1H, bs).

Example 3
Compound (I)

An oxygen free solution of 2-trifluoromethane-sulphonyloxy-4-benzyloxy-5-[(5-methyl-2H-pyrrol-2-ylidene)methyl]-1H-pyrrole (6.0 g; 14.70 mmols) in dioxane (350 ml) was treated in sequence, under argon atmosphere, with (1-t-butoxycarbonyl-pyrrol-2-yl)boronic acid (12.4 g; 58.78 mmols), potassium carbonate (16.24 g; 117.57 mmols), tetrakis(triphenylphosphine)palladium(0) (849 mg; 0.734 mmols) and heated to 95° C., under stirring, for 5 hours. After cooling, the reaction mixture was poured into ice-water (400 ml) and extracted with ethyl acetate (3×300 ml). The organic phase was shaken with water and brine, anhydrified over anhydrous sodium sulphate, filtered and evaporated to dryness in vacuum. The residue was purified over a short Al$_2$O$_3$ column (activity II–III) using hexane/ ethyl acetate 3/1 as eluant. The collected fractions were concentrated, dissolved in ethyl ether, treated with a solution of hydrochloric acid in isopropyl ether at 5° C. and, after stirring for 30 minutes, filtered to give 4-benzyloxy-5-[(5-methyl-2H-pyrrol-2-ylidene)methyl]-2,2'-bi-1H-pyrrole, hydrochloride (2.54 g; 6.94 mmols). Yield: 47%.

$^1$NMR (400 mhz, CDCl$_3$), ppm: 2.56 (3H, s), 5.22 (2H, s), 6.15 (1H, d, J=1.7 Hz), 6.18 (1H, dd, J=4.0, 1.8 Hz), 6.37 (1H, m), 6.83 (1H, dd, J=4.0, 2.4 Hz), 6.94 (1H, m), 7.06 (1H, s), 7.26 (1H, m), 7.45 (5H, m), 12.65 (1H, bs), 12.81 (1H, bs), 12.85 (1H, bs).

By analogous procedure the following compounds can be synthesized:

4-benzyloxy-5-[(5-pentyl-2H-pyrrol-2-ylidene)methyl]-2,2'-bi-1H-pyrrole, hydrochloride $^1$NMR (400 mhz, CDCl$_3$), ppm: 0.90 (3H, m), 1.38 (4H, m), 1.78 (2H, m), 2.95 (2H, t), 5.22 2H, s), 6.15 (1H, d, J=1.8 Hz), 6.20 (1H, dd, J=4.0, 1.8 Hz), 6.36 (1H, m), 6.84 (1H, dd, J=4.0, 3.0 Hz), 6.94 (1H, m), 7.06 (1H, s), 7.24 (1H, m), 7.44 (5H, m), 12.68 (1H, bs), 12.75 (1H, bs), 12.93 (1H, bs).

4-benzyloxy-5-[(5-ethyl-2H-pyrrol-2-ylidene)methyl]-2,2'-bi-1H-pyrrole, hydrochloride $^1$H-NMR (400 Mhz, CDCl$_3$), ppm: 1.36 (3H, t, J=7.6 Hz), 2.99 (2H, q, J=7.6 Hz), 5.22 (2H, s, ), 6.14 (1H, d, J=1.5 Hz), 6.22 (1H, dd, J=3.9, 1.4 Hz), 6.36 (1H, m), 6.85 (1H, dd, J=3.9, 2.7 Hz), 6.94 (1H, m), 7.06 (1H, s), 7.26 (1H, m), 7.45 (H, m), 12.6 (1H, bs), 12.7 (1H, bs), 12.8 (1H, bs);

4-benzyloxy-5-[(5-propyl-2H-pyrrol-2-ylidene)methyl]-2,2'-bi-1H-pyrrole, hydrochloride;
4-benzyloxy-5-[(5-isopropyl-2H-pyrrol-2-ylidene)methyl]-2,2'-bi-1H-pyrrole, hydrochloride;
4-benzyloxy-5-[(5-butyl-2H-pyrrol-2-ylidene)methyl]-2,2'-bi-1H-pyrrole, hydrochloride;
5'-methyl-4-benzyloxy-5-[(5-methyl-2H-pyrrol-2-ylidene)methyl]-2,2'-bi-1H-pyrrole, hydrochloride;
5'-methyl-4-benzyloxy-5-[(5-ethyl-2H-pyrrol-2-ylidene)methyl]-2,2'-bi-1H-pyrrole, hydrochloride;

Example 4
Formulation: Capsules (150 mg)

Capsules, each weighing 400 mg and containing 150 mg of the active substance, are manufactured as follows.

Composition

| | |
|---|---|
| 4-benzyloxy-5-[(5-methyl-2H-pyrrol-2-ylidene)methyl]-2,2'-bi-1H-pyrrole, hydrochloride | 150 mg |
| Lactose | 198 mg |
| Corn starch | 50 mg |
| Magnesium stearate | 2 mg |
| Total | 400 mg |

Encapsulated in two-piece hard gelatin capsules.

What is claimed is:

1. A compound which is a prodigiosine of formula (I)

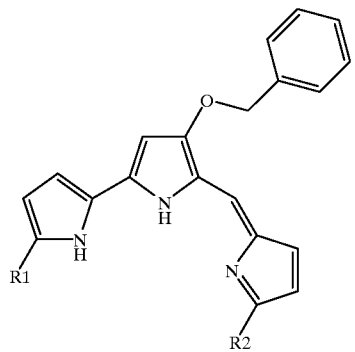

(I)

wherein
  R1 is hydrogen or C$_1$–C$_5$ alkyl; and
  R2 is C$_1$–C$_5$ alkyl;
or a pharmaceutically acceptable salt thereof.

2. A compound according to claim 1, wherein
  R1 is hydrogen or methyl; and
  R2 is a C$_1$–C$_5$ alkyl.

3. A compound selected from:

4-benzyloxy-5-[(5-methyl-2H-pyrrol-2-ylidene)methyl]-2,2'-bi-1H-pyrrole;
4-benzyloxy-5-[(5-ethyl-2H-pyrrol-2-ylidene)methyl]-2,2'-bi-1H-pyrrole;
4-benzyloxy-5-[(5-propyl-2H-pyrrol-2-ylidene)methyl]-2,2'-bi-1H-pyrrole;
4-benzyloxy-5-[(5-isopropyl-2H-pyrrol-2-ylidene)methyl]-2,2'-bi-1H-pyrrole;
4-benzyloxy-5-[(5-butyl-2H-pyrrol-2-ylidene)methyl]-2,2'-bi-1H-pyrrole;
4-benzyloxy-5-[(5-pentyl-2H-pyrrol-2-ylidene)methyl]-2,2'-bi-1H-pyrrole;
5'-methyl-4-benzyloxy-5-[(5-methyl-2H-pyrrol-2-ylidene)methyl]-2,2'-bi-1H-pyrrole;
5'-methyl-4-benzyloxy-5-[(5-ethyl-2H-pyrrol-2-ylidene)methyl]-2,2'-bi-1H-pyrrole;
and the pharmaceutically acceptable salts thereof.

4. A compound according to claim 3 which is a hydrochloride, hydrobromide or methanesulphonate salt.

5. A pharmaceutical composition comprising a pharmaceutically acceptable carrier and/or diluent and, as an active principle, a compound as defined in claim 1.

6. A pharmaceutical composition for use in immunosuppressive therapy in a mammal, comprising:
  (a) an immunosuppressive agent in a pharmaceutically acceptable carrier and/or excipient, and
  (b) at least one compound as defined in claim 1 in a pharmaceutically acceptable carrier and/or excipient, in amounts to produce a superadditive immunosuppressant effect.

7. A product containing a compound as defined in claim 1, and an anti-tumor agent as a combined preparation for use in adult-T-cell leukemia-lymphoma therapy.

8. A method of treating a mammal suffering from adult-T-cell leukemia-lymphoma, which method comprises administering to said mammal a therapeutically effective amount of a compound as defined in claim 1.

9. An immunosuppressive therapy method for use in a mammal in need thereof, which method comprises administering to the mammal (a) an immunosuppressive agent and (b) at least one compound as defined in claim 1, in amounts effective to produce a superadditive immunosuppressive effect.

10. A method for lowering the side effects caused by immunosuppressive therapy with an immunosuppressive agent in a mammal in need thereof, which method comprises administering to said mammal a combination preparation comprising (a) said immunosuppressive agent and (b) at least one compound as defined in claim 1 in a quantity effective to produce a superadditive immunosuppressive effect.

11. A combined method of treatment of adult-T-cell leukemia-lymphoma in a mammal in need thereof, which method comprises administering thereto a compound as defined in claim 1, and an anti-tumor agent, in amounts and close enough together in time sufficient to produce a therapeutically useful effect.

12. A method of treating a mammal in need of an immunomodulating agent, which method comprises administering to said mammal an effective amount of a compound as defined in claim 1.

13. A method for treatment of graft-versus-host diseases in a mammal, which method comprises administering to said mammal an effective amount of a compound as defined in claim 1.

14. A method for treatment of autoimmune diseases in a mammal, which method comprises administering to said mammal an effective amount of a compound as defined in claim 1.

* * * * *

UNITED STATES PATENT AND TRADEMARK OFFICE
CERTIFICATE OF CORRECTION

PATENT NO. : 6,369,096 B1  Page 1 of 1
DATED : April 9, 2002
INVENTOR(S) : D'Alessio et al.

It is certified that error appears in the above-identified patent and that said Letters Patent is hereby corrected as shown below:

<u>Title page,</u>
Item [87], PCT information should read as follows:
-- [87] PCT Pub. No.: WO99/40069
PCT Pub. Date: Aug. 12, 1999 --

Signed and Sealed this

Twenty-ninth Day of October, 2002

Attest:

Attesting Officer

JAMES E. ROGAN
*Director of the United States Patent and Trademark Office*